US005636024A

United States Patent [19]
Crookham et al.

[11] Patent Number: 5,636,024
[45] Date of Patent: Jun. 3, 1997

[54] APPARATUS AND METHOD OF INSPECTION OF SPECULAR AND SEMI-SPECULAR SURFACES

[75] Inventors: Joe P. Crookham, Oskaloosa; Mark A. DeJong, Eddyville; George P. Glass, Oskaloosa, all of Iowa

[73] Assignee: Musco Corporation, Oskaloosa, Iowa

[21] Appl. No.: 710,087

[22] Filed: Sep. 10, 1996

Related U.S. Application Data

[63] Continuation of Ser. No. 318,280, Oct. 5, 1994, abandoned.

[51] Int. Cl.⁶ .................................................. G01N 21/00
[52] U.S. Cl. ............................................ 356/371; 356/237
[58] Field of Search ................................ 356/237, 371, 356/376

[56] References Cited

U.S. PATENT DOCUMENTS

| | | | |
|---|---|---|---|
| 2,707,415 | 5/1955 | Rooney, Jr. | 356/446 |
| 3,609,044 | 9/1971 | Murphy | 356/446 |
| 3,925,049 | 12/1975 | Schwenninger | 356/430 |
| 4,065,213 | 12/1977 | Nyman | 356/430 |
| 4,392,187 | 7/1983 | Bornhorst | 362/233 |
| 4,533,245 | 8/1985 | Love, III | 356/238 |
| 4,629,319 | 12/1986 | Clarke et al. | 356/237 |
| 4,714,340 | 12/1987 | Stillwagon | 356/430 |
| 4,738,538 | 4/1988 | Hearst | 356/446 |
| 4,886,355 | 12/1989 | Keane | 356/445 |
| 4,918,321 | 4/1990 | Klenk et al. | 250/571 |
| 4,989,984 | 2/1991 | Salinger | 356/445 |
| 5,092,676 | 3/1992 | Harata et al. | 356/371 |
| 5,141,320 | 8/1992 | Harata et al. | 356/371 |
| 5,142,648 | 8/1992 | Fitts et al. | 364/551 |
| 5,153,445 | 10/1992 | Stapleton | 250/572 |
| 5,179,425 | 1/1993 | Reinsch et al. | 356/371 |
| 5,208,766 | 5/1993 | Chang et al. | 364/552 |
| 5,249,029 | 9/1993 | Sommer et al. | 356/336 |
| 5,367,378 | 11/1994 | Harding et al. | 356/376 |
| 5,436,726 | 7/1995 | Ventura et al. | 356/371 |

OTHER PUBLICATIONS

Photograph of Existing Paint Inspection Station (Date: Precedes Filing Date of Present Application) (no date).

*Primary Examiner*—Richard A. Rosenberger
*Attorney, Agent, or Firm*—Zarley, McKee, Thomte, Voorhees, & Sease

[57] ABSTRACT

An inspection apparatus and method for specular and semi-specular surfaces include a supporting floor and surrounding background which is non-reflective and light absorbing, such as flat black. Portions of the background and/or floor are illuminated either by allowing translucent passage of light from behind or by illuminating a somewhat reflective but light diffusing surface. The reflected images of the illuminated portions can be viewed in the object being inspected, such as a painted car body in an automobile manufacturing line. Ambient light and direct light to the car body is kept to a minimum. Therefore, a high amount of contrast exists between the reflected images of the illuminated portions and those portions of the car body which reflect the dark background. Geometrical shapes can be used for the illuminated portions to assist in an inspection of the auto body.

38 Claims, 4 Drawing Sheets

APPARATUS AND METHOD OF INSPECTION OF SPECULAR AND SEMI-SPECULAR SURFACES

This is a continuation Ser. No. 08/318,280 filed on Oct. 5, 1994 now abandoned.

BACKGROUND OF THE INVENTION

A. Field of the Invention

This invention relates to inspection for flaws of any surface that is smooth enough to provide a reflection. One particular example is surfaces such as painted surfaces on such things as, for example, automobile bodies and the like where the paint or the underlying surface are inspected for flaws, the invention relates to both an apparatus and method by which such inspections takes place, including but not limited to along an automated production line.

B. Problems in the Art

Most automobile manufacturers use robotics and an automated painting system to apply various coats of paint to create the paint surface on the automobile bodies that are then used to create the complete automobile. While such systems generally perform satisfactorily, most manufacturers have a quality review of the paint job prior to approving the painted car body for assembly into the completed car.

One conventional quality control review involves workers manually moving around each automobile body as it moves along a conveyor and visually scanning the automobile body for a number of different possible flaws.

The workers are generally given only a short time (for example only several minutes) to evaluate the entire automobile body. Generally, the industry has constructed a paint inspection station that has sufficient room for the workers to walk around each car body. Importantly, the state of the art provides as much direct light as possible to the car bodies during the inspection process. The theory is apparently that the more light the better to visually identify flaws. The emphasis is on lighting the car body.

The inspection workers must watch for as many as several tens of different types of flaws or defects. For example, if there is an underlying flaw such as a raised portion or recessed portion in the car body metal, this will normally be reflected in a raised or recessed portion respectively in the paint job. Also, such things as dust or other particles that may have settled on the car body prior to or during painting will result in a noticeable flaw.

Presently, automobile paint jobs are multi-coat. For example, a first coat or a neutral color rust inhibitor of fairly matte finish (sometimes called an "E" coat), is applied to the metal. A primer coat, usually neutral with a somewhat matte finish or the same color as the ultimate car color, is applied to the first coat. Finally, one or more top coats, for example, a base coat plus a clear coat can be applied over the primer coat.

The inspector analyzes the first coat for such things as uniformity, flaws and foreign materials. The primer coat is analyzed for such things as flaws, eveness, uniformity, dirt, cavities, runs, and negative or positive depressions in the metal. The top coat creates a highly reflective surface which is inspected for such things as eveness, white spots, striations, swirl marks and other flaws.

If a flaw is identified, the workers attempt to polish it out on the spot, or the car body must be towed from the assembly line to another location for paint repair. It should be understood that if the repairs are substantial, whole sections of the body may have to be repainted. When the body is then passed again through the paint inspection station, a further important evaluation involves whether the repainted portion matches the rest of the car with respect to color, in addition to looking for the other flaws and for blending and eveness.

Bathing the car bodies in light does arguably help in identifying certain flaws, but the problems with such an approach include the following. To bathe the car body in so much direct light with so many fixtures adjacent the car body can wash out or minimize the visual perception of certain flaws. Additionally, glare from light fixtures that are projecting light towards the inspector can reduce the ability to accurately analyze the paint job. Moreover, reflections of the fixture's direct light from the car body makes it many times difficult to identify flaws and can cause glare and difficulty in concentrating on the inspection and upon insuring that all portions of the car body are examined carefully.

Moreover, so much direct light can also make it very difficult to analyze color matching. With clear coated paint jobs, the highly reflective nature of the paint coating increases the problems of having so much direct light to the car body. Also, by bathing the entire paint inspection area in light, it eliminates any contrast between the car body and the surrounding areas.

Several United States patents exist which address the issue of inspecting paint jobs. U.S. Pat. No. 4,918,321 to Klenk, et al. discloses a completely automated inspection system. Live inspectors are not used. Sensors, including video cameras, receive reflected light from the vehicle surface and a computer controls a scanning mirror so that the vehicle body is essentially scanned for flaws. The computer must analyze the video image. Direct light is provided to the vehicle body.

U.S. Pat. No. 3,609,044 to Murphy is an apparatus for inspection of a specular surface and a coating on the surface. A reference pattern is projected onto the surface being inspected for detection of defects. In this instance light through the projected pattern is directly sent to the object's surface.

U.S. Pat. No. 4,629,319 to Clarke, et al. also utilizes the projection of a grid of light to a panel for detection of defects in sheet metal or plastic panels.

As previously discussed, the method of projecting light directly to the object being inspected carries with it deficiencies which impact upon the accuracy of the inspection. It is therefore a principle object of the present invention to provide an apparatus and method for paint inspection which improves over or solves the problems and deficiencies in the art.

Objects of the Invention Include:

1. Reduction of glare during the inspection process.

2. Reduction in the amount of light and illumination directly to the object of inspection and, in fact, intentionally removing direct light to the object and reducing ambient light.

3. Allowance of improved inspection for the variety of flaw types.

4. Allowance for inspection of different colors and types of paint jobs.

5. Assistance in the ability to concentrate and comprehensively cover the entire surface of the object under inspection.

6. Reduction in any washing out or lack of contrast between the object being inspected and the surroundings.

7. An economical setup in terms of both material, operating, and labor costs.

8. A flexible and adjustable system for different objects and coatings including different object shapes.

These and other objects, features, and advantages of the present invention will become more apparent with reference to the accompanying specification and claims.

SUMMARY OF THE INVENTION

The present invention utilizes a paint inspection station, which both reduces as much as possible any ambient and direct light around or to the object under inspection and presents a dark background to the object under inspection. Portions of the background surrounding the object under inspection are illuminated in a manner such that inspectors can view the reflections of those illuminated portions in the object under inspection. Therefore, there is minimal direct lighting of the object which reduces glare and any washing out of the object, and the predominately dark background provides a high contrast to the object being inspected.

One feature of the invention involves utilizing the illuminated portions of the background in a geometric pattern. The reflection of the geometric pattern in the object allows the viewer to have a controlled reference shape to use in the evaluation of the surface of the object. When an illuminated portion reflects off a flaw in the surface of the object, the geometric pattern becomes noticeably distorted. The illuminated sections can be spaced or oriented towards the object to allow a reflection of the illuminated sections to be easily visually accessible by the inspector in all the normal positions the inspector will take when inspecting the object. The reference shape can also be oriented to best be used with a specific shape or curvature of the object under inspection.

According to another aspect of the invention, the intensity of the illuminated sections can be controlled in relation to factors including, for example, the amount of ambient light, the color of the object being inspected, the type of object being inspected, and other factors. Similarly, the size of the illuminated sections, any pattern formed by the illuminated sections, and even the color of the illumination can be controlled. Other adjustments can be made to benefit a comprehensive and accurate analysis of the object under inspection.

DETAILED DESCRIPTION OF A PREFERRED EMBODIMENT

A. Overview

To better understand the invention, a detailed description of a preferred embodiment will now be set forth. It is to be understood that the description of this preferred embodiment is only an example of one form the invention can take and is not comprehensive or inclusive of all the different forms the invention can take.

Frequent reference will be taken in this description to the drawings. Reference numbers are utilized to indicate certain parts and locations in the drawings. The same reference numerals will indicate the same parts or locations in all the drawings unless otherwise indicated.

A brief description of a conventional existing paint inspection station for automobiles will first be set forth. The structure of an embodiment according to the invention will then be described followed by a discussion of its operation. Finally, examples of alternatives and options for the invention will be discussed.

It is to be understood that prior discussion as well as discussion in this detailed description focus upon inspecting paint jobs on automobile bodies in the manufacturing process, but that the application of these concepts to the inspection of other objects, coatings, or surfaces for other purposes can be well appreciated. For example, in certain fine wood products such as furniture, inspection of varnish or other coatings may be used advantageously with the invention. Furthermore, inspection of a wide variety of surfaces, whether painted, coated, or not, for flaws or uniformity can be accomplished with the invention. The only requirement is that the inspected surface allow a reflection, that is, be specular or semi-specular, not diffuse or non-reflective.

B. Conventional Paint Inspection Methods

Figure 1:
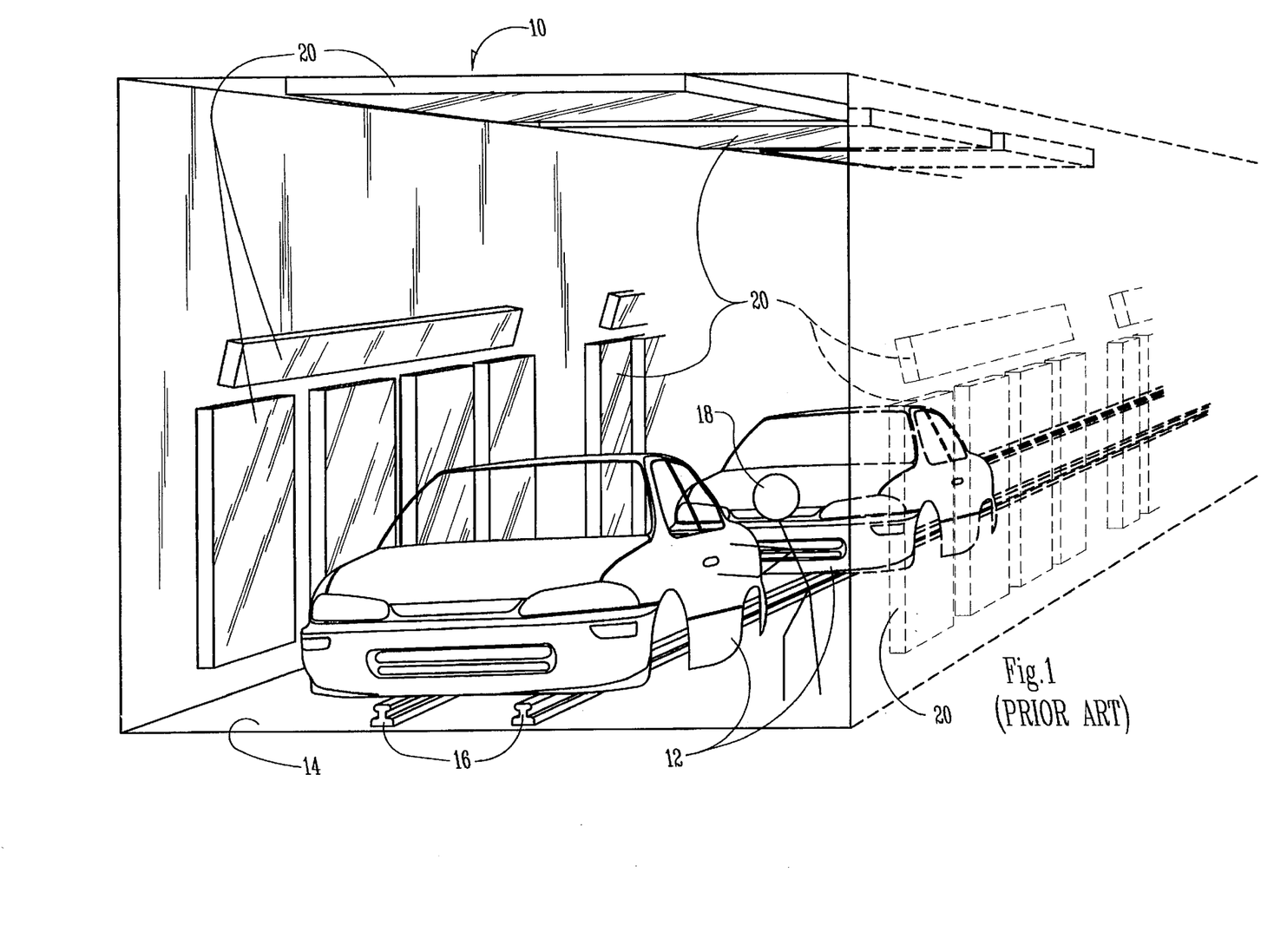
FIG. 1 is a perspective diagrammatic depiction of a prior art paint inspection station.

FIG. 1 diagrammatically illustrates a widely used paint inspection method for auto bodies 12. By referring to FIG. 1, prior art paint inspection station 10 has a floor 14 along which a track 16 extends. Auto bodies 12, by means well known in the art, are moveable along track 16. Worker 18 (generally there are at least two) has space to walk around and between bodies 12 to inspect at least certain exterior painted surfaces for flaws.

The primary concept of station 10 is the utilization of a plurality of lights 20 to essentially bathe and permeate station 10 with light. Moreover, station 10 intentionally directs a substantial amount of light to the car bodies. By doing so, the rationale is that all surfaces of each body 12 will be highly lighted by creating a high light level throughout station 10, to allow the best inspection and visual identification of flaws by worker 18.

As can be seen in FIG. 1, the plurality of lights 20 literally include adjacent vertically extending lights along the side walls of station 10, end to end lights angled downwardly toward the roof of bodies 12 on each side wall, and lateral lights across the ceiling of station 10. There are basically walls of lights surrounding the car bodies 12. Worker 18 therefore in most instances will have light from at least one fixture 20 traveling in the direction of the worker's eyes (or reflecting into the worker's eyes) no matter what side or position worker 18 has relative to body 12.

C. Embodiment of FIG. 2

Figure 2:
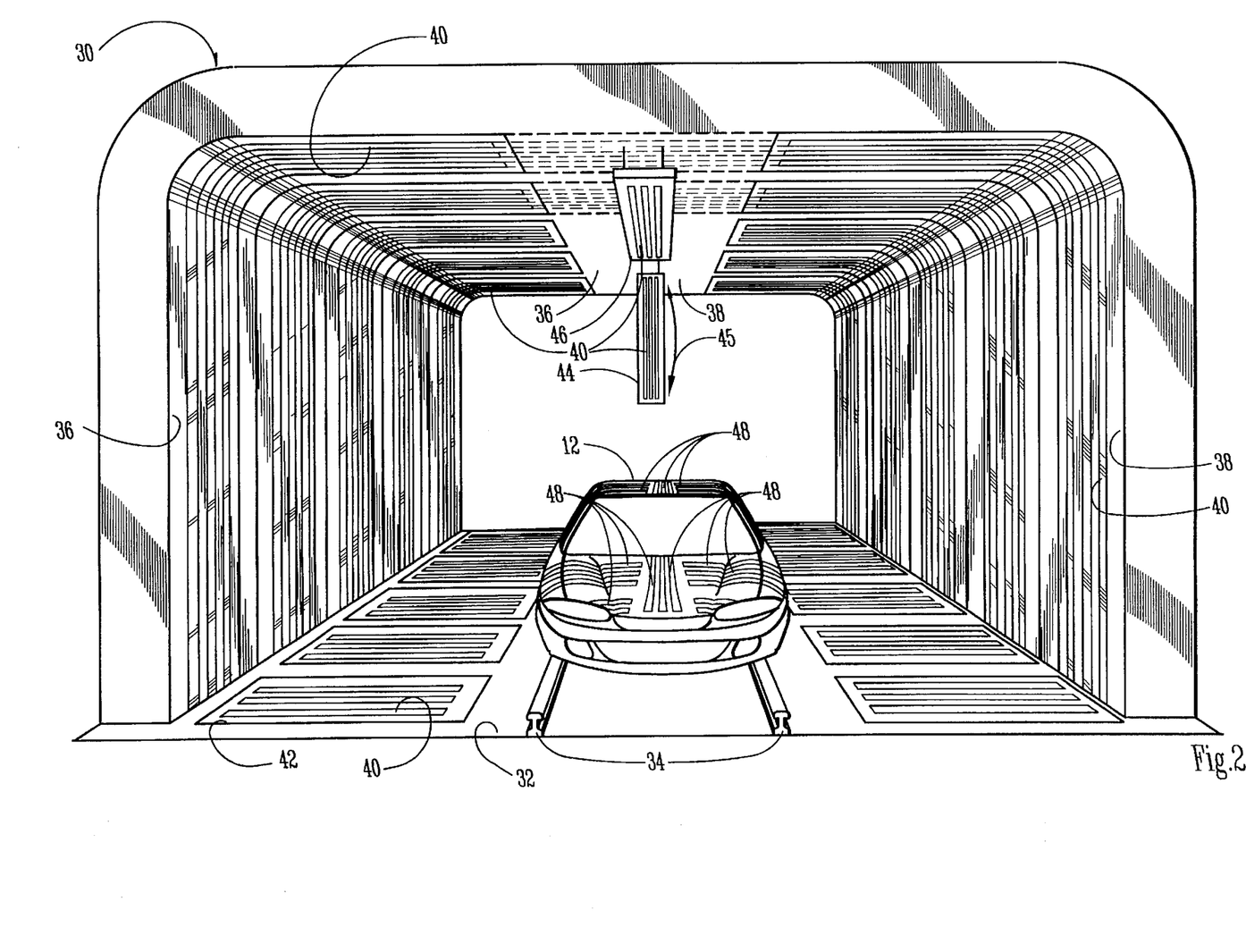
FIG. 2 is a perspective depiction of a paint inspection station according to an embodiment of the present invention.

FIG. 2 shows paint inspection station 30 according to the preferred embodiment of the present invention. A floor or support surface 32 can have tracks 34 or some other structure along which objects to be inspected can be moved. In this instance tracks 34 can be essentially the same as tracks 16 of FIG. 1. Obviously, however, tracks 34 are not essential to operation of station 30 or the function of moving objects into, through, and out of station 30 can take many different forms and is not a part of this invention.

In distinction to station 10, station 30 utilizes essentially a shroud or canopy. As can be seen in FIG. 2, side walls 36 and 38 extend upwardly from opposite sides of floor 32 and then converge inwardly to provide a substantial enclosure of floor 32. It is to be understood that in the preferred embodiment, floor 32 as well as side walls 36 and 38 are painted or otherwise made to be non-reflective and light absorbing, to the extent possible. For example, they can be painted with a very matte black paint. In certain circumstances floor 32 may be a grate which is painted black matte. To the extent possible, the areas underneath floor 32 also would be as non-reflective and light absorbing as possible. Moreover, any gaps between the converging top edges of side walls 36 and 38 would be made as non-reflective and light absorbing as possible.

It is preferred that ambient light inside station 30 be minimized, at least as much as possible. Also, to the extent possible, ambient light around station 30 is preferred to be minimized. End walls or curtains (not shown) could also be used to either fully or partially close the ends of station 30. Of course, any gaps of whatever nature could also be covered or otherwise steps taken to reduce the introduction of ambient light and to essentially black out the entire background along tracks 34. Alternatively, the room in which station 30 is positioned could be darkened.

FIG. 2 illustrates that in the preferred embodiment, several areas or portions of floor 32 and side walls 36 and 38 exist (see reference numerals 40) which essentially take the form of strips or stripes. In the preferred embodiment, portions 40 are translucent, or at least partially light transmissive, sections behind which a light source (not shown) is placed. Portions 40 would permit a certain amount of light to come through but would be configured to diffuse the light that passes through them. Essentially, they would represent illuminated (or luminous) stripes that would not pass much direct light to the car bodies being inspected and would not create a great deal of ambient light within station 30, but rather would be used to cause reflected images of the stripes to be formed in the car bodies. The stripes are usually preferred to have very defined edges so that reflected images of the stripes have very defined edge. Thus, the ambient light inside station 30 would normally be minimal and the reflections would allow the inspectors to have a clear but contrasted image to use to inspect the surface of the car bodies.

It is to be understood that the edges of the illuminated pattern (here the stripes) could be very defined in the sense that each stripe has a very distinct straight edge on both sides. Alternatively, the illuminated pattern could have a defined edge characteristic; such as, for example, a curved edge, a repeating geometrical shape, or a non-repeating shape. The edge does not necessarily have to be continuous and may take many shapes and forms.

In the embodiment of FIG. 2, side walls 36 and 38 can be formed out of sheet material. clear acrylic or plastic sheet, glass, metal sheet or any material which can be painted flat black could be used. Metal sheet, and particularly aluminum, is advantageous because it is easy to fabricate into needed shapes.

One way to construct side walls 36 and 38 is to make the entire wall 36 and the entire wall 38 out of one sheet of clear acrylic. The entire sheet is sand blasted to provide a very light diffusing surface. All areas except portions 40 are painted with black matte paint. Portions 40 are left alone and light sources are placed behind (on the opposite side of walls 36 and 38 from car bodies 12) portions 40 to illuminate them. In the preferred embodiment fluorescent lights are used and extend basically along the length of the stripes. Fluorescent lights were chosen primarily because of their low profile (in other words, they can be placed right behind the stripes and do not take up much room relative to extending away from the sidewalls). However, many different light sources would function. It is preferred that the light source function to uniformly apply light.

In this embodiment, panels 42 with illuminated portions 40 are placed along floor 32 (in this case can be a grated floor). If panels 42 are made from clear acrylic sheet, they can again be sand-blasted and all but portions 40 painted flat black. An option, to make the light more uniform and diffuse from portions 40, is to use two panels 42A and 42B (see FIG. 4) preferably placed one over the other (for example, 2 inches apart). Each panel 42A and 42B is sand-blasted so that light passing through two panels is diffused more than if it passed through one panel only. In the preferred embodiment, only top-most panel 42a has portions 40 (with the remainder painted flat black). Panel 42b functions solely as a light diffuser panel.

If the light source is sufficiently uniform however, only one panel 42 might be needed. Also, if sheet metal is used, for example, for panel 42, sand-blasted clear acrylic strips could be used for portions 40, inlaid into appropriately sized cut-outs in the sheet metal.

FIG. 2 also shows that additionally panels 44 and 46 can be, for example, placed in a suspended position above tracks 34. Panel 44 could be useful for providing illuminated portions 40 for a sloped trunk, for example, and could even be tilted to approximate the slope of the trunk, if any. Arrow 45 in FIG. 2 is intended to indicate that panel 44 could be swung down into position at a variety of different angles, and could also be swung up, parallel with the position of panel 46.

Panel 46 could be used to provide illuminated portions 40 to the roof and/or hood of car body 12, for example. Other panels, such as a separate panel suspended over the hood of car body 12, could be used. The precise shape, dimensions, position and number of panels such as 44 and 46 can vary according to needs and circumstances.

Figure 3:
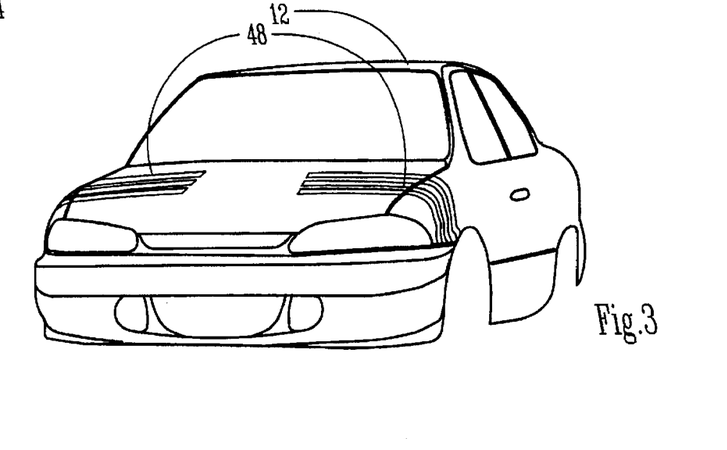
FIG. 3 is a perspective view of an object under inspection according to the embodiment of FIG. 2.

FIGS. 2 and 3 graphically depict the reflections 48, in this embodiment, comprising multiple sets of three stripes of illuminated portions 40. These two views illustrate an important point related to this embodiment. A paint inspector will, at any one time, have one view angle to car body 12. The inspector will only be able to see a part of body 12. Therefore, in this embodiment, multiple sets of stripes (portions 40) are distributed in positions all around (and even over) car body 12. They are configured so that the inspector can have parallel reflections along each of the various portions of body 12 (e.g. door, quarter panels, fenders, trunk, roof, hood). Therefore, if the inspector is at the view angle of FIG. 2, he/she might be able to see reflections 48 for both sides of the hood, and a part of reflections 48 for the roof, as he/she moves around the car to a position such as FIG. 3, less of the car body 12 and less of portions 40 will be seen.

Although it is to be understood that by basic reflection laws, e.g. angle of incidence versus angle of reflection, reflections 48 will travel at least a little distance with inspector 18 as the inspector moves around car body 12, and that this actually helps in inspecting the car surface at those locations, such movement is quite limited. Therefore, different sets of illuminated portions 40 are positioned relative to different portions of the car body so that a set will be available for all locations on the car body that are desired to be inspected. In other words, a set reflections will be directly available for each area of car body 12 as the inspector(s) move around it.

The illuminated patterns are positioned relative to both the object being inspected and the inspector (or viewer) so that an illuminated pattern is reflected in the surface of the object at an angle or angles incident to the viewer to allow use of the pattern in the inspection process.

It is to be understood that most car bodies 12 have substantially curved surfaces. Therefore, it is beneficial to have sets of illuminated portions 40 for such things as the trunk, roof, hood, and side walls of body 12, as well as lower side walls of body 12. It has been found that it is preferred that the stripes of reflections 48 normally travel in the direction of curvature of the portion of body 12, and therefore the sets of illuminated portions 40 of side walls 36 and 38 and of panels 42 are configured to travel in planes that are more transverse to the longitudinal axis of car body 12 (which is parallel with tracks 34) In comparison, portions 40 of panels 44 and 46 run generally along the longitudinal axis of car body 12, because trunks and roofs tend to curve along that axis. Also, it is desirable and preferable if possible to have all illuminated portions follow a smooth curve (instead of making sharp corners). By doing so there will not be sharp changes in direction of reflections 48 in car body 12, which would make inspection harder. For example, note in FIG. 2 that walls 36 and 38 are gently curved coverage over car bodies 12. This creates smooth transitions in reflections 48.

FIGS. 4–7 show the interior construction of the components to cause illumination of portions 40 and panel 42. Fluorescent bulbs 60 are placed in reflectors 62 which can be attached directly behind portions 40 (the term "behind" meaning on the opposite side of walls 36 and 38 from the interior of station 30). Reflectors 62 enclose lamps 60 and substantially prevent any light from escaping outside of reflector 62. In this embodiment, reflectors 62 are generally rectangular in cross-section aluminum sheet covers placed over each set of portions 40. It is noted that in this embodiment, longer lamps 60 are used from floor 32 upward until reflector 62 starts to bend inwardly. Shorter lamps 60 are used to make the turn to the horizontal lamp so that lamps 60 can provide uniform light along the entire illuminated portions 40; even at the curve. An optional feature would be an intensity control 64 to control the intensity of light output from lamps 60. The ends of lamps 60 overlap to compensate for the non-light-emitting parts (such as socket), as well as about the first one inch of the glass part of each lamp inward from the socket.

Figure 4:
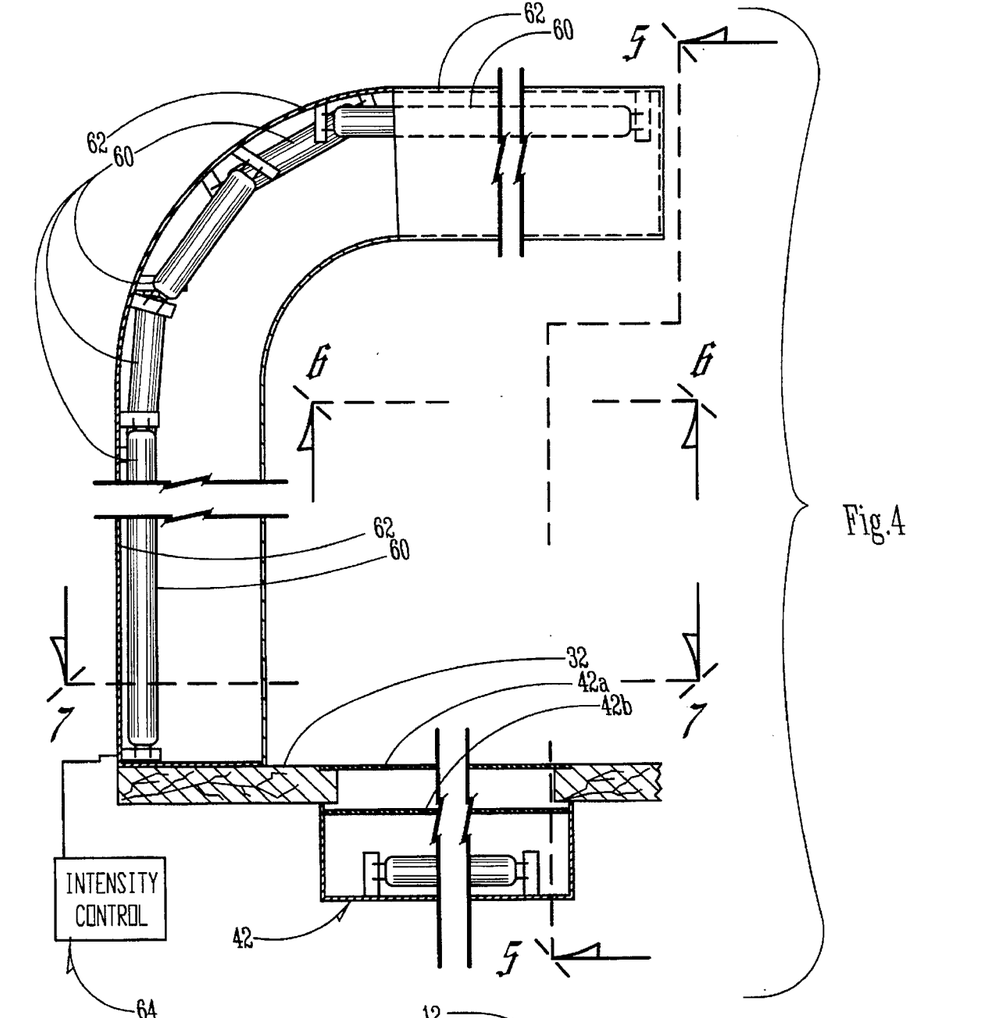
FIG. 4 is an enlarged sectional elevational view of a portion of the embodiment of FIG. 2.
Figure 5:
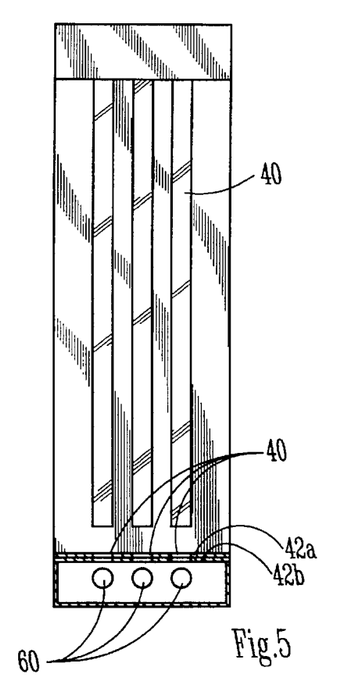
FIG. 5 is a sectional view taken along line 5—5 of FIG. 4.
Figure 6:
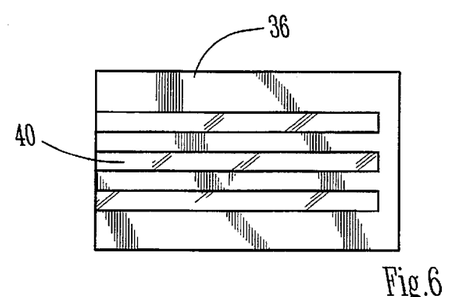
FIG. 6 is a sectional view taken along line 6—6 of FIG. 4.
Figure 7:
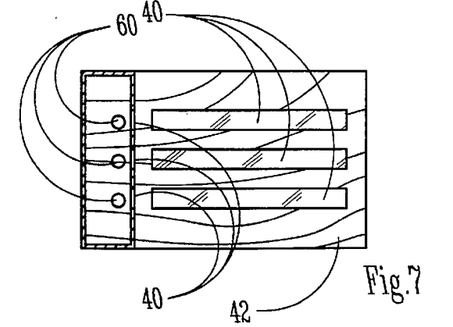
FIG. 7 is a sectional view taken along line 7—7 of FIG. 4.

FIGS. 4 and 5 also illustrate the double panels 42A and 42B that are possible in the floor mounted panel 42 and shows fluorescence lamp 60 and a reflective enclosure 62 similar to that previously described. It is to be understood that the mounts and connections to an electrical power source for lamps 60 is not shown in detail but is within the skill of one skilled in the art to make and use.

FIGS. 4–7 therefore show with more detail how the illuminated portions 40 provide illuminated areas of station 30 which are used to form the reflected images 48 in the auto bodies 12. The area of illuminated portions 40 is substantially less than the area of the flat black surroundings. Portions 40 pass diffuse light. Therefore, by using strips of illumination (reference numerals 40) surrounding car body 12, the amount of ambient light and the amount of direct light to body 12 is minimized.

D. Operation

By referring particularly to FIGS. 2–4, fluorescent lamps 60 are turned on to create illuminated portions 40. Auto bodies 12 are then brought into station 30. The inspectors scan the surface of auto body 12 and move around auto body 12 using reflections 48 (see FIG. 3) to view various sections of the surface of body 12 for flaws. Because reflections 48 do not represent a large amount of direct light, they do not wash out or minimize the visual perception of flaws or the surface of body 12 or provide a detrimental amount of glare to the inspector's eye. Also, it is to be understood that if stripes are used as illuminated portions 40, such as shown in the described embodiment, the edges of the stripes function as straight edges between the dark areas and the reflections 48 to further assist in analysis of surface of body 12. When an illuminated stripe reflects off an irregularity in the surface of the body 12, the stripe becomes noticeably distorted due to basic laws of reflection. For example, striations or surface discontinuities show up well when measured against the edges of stripe reflections 48.

By moving relative to body 12, reflections 48 also move slightly as previously described. Thus, slight movements of the inspectors head can allow use of stripe reflections 48 to move those straight edges along surface of body 12.

It is emphasized that the illuminated portions can be accomplished by different methods, but it is to be understood that it is those portions, and not the object being inspected, that are illuminated. Another way to describe this is to think of those portions as being luminous, whether by backlighting, front lighting, or otherwise (such as, for example, using a material that has luminescence), and that those luminous portions are reflected by the object being inspected. The reflections in the object being inspected thus help the inspection process as previously discussed. There is not direct illumination of the object being inspected, rather the luminous portions are reflected in the object.

E. Alternatives, Features, and Options

To further assist in an understanding of the invention, several features, alternatives, and options according to the present invention will now be described. It is to be understood that the following description also does not limit the scope of the invention.

To further eliminate ambient light and to increase concentration of inspection on certain portions of body 12, certain of lamps 60 could be turned off. For example, when inspecting one side of body 12, the opposite side illuminated portions 40 could be turned off. More control could be accomplished by sequentially turning on a set or sets of illuminated portions 40 which are relevant to that area of inspection as the inspector moves along the car.

Intensity of the illuminated portions can also be controlled. For example, if for whatever reason more ambient light is present than normal or than desired, the intensity of lamps 60 might be increased to maintain a good level of contrast between reflections 48 and the reflection of the background of station 30. Likewise, intensity could be reduced if desired or needed, as an option. It is to be understood that in certain circumstances higher or lower intensities provide better contrast or analysis, for example, depending on color or specularity of the inspected surface.

Reference lines could be created. For example, a horizontal illuminated portion could be placed along a set of vertical illuminated stripes (or the vertical stripes could be broken up along their length) to create a reference line reflection in body 12. Such things may help an inspector focus on certain sections so the inspector does not repeat or miss the inspection of a section of the car body.

Furthermore, it is to be understood that the size and shape of any reflected portion 40 can be varied according to need or desire. In the present preferred embodiment, illuminated portions 40 are approximately 2 inches wide and are configured in sets of three illuminated portions 40 separated by two dark portions of the same width (see FIGS. 5–7). In the preferred embodiment, 130 foot candles of light intensity is provided at the surface of side walls 36 and 38 at illuminated portions 40. This of course can vary. It is to be understood that different intensities of light can be desirable for different situations. Some of the factors involved include nature of the finish on the inspected surface, nature of the flaws, amount of ambient light, and color of the inspected surface. Other factors are possible depending on the circumstances. For example, if 120 foot candles of light exist at side walls 36 and 38, this might translate into approximately 12 foot candles at the surface of car body 12 for certain light sources and materials for portions 40. This may be enough for inspecting clear coats (which are highly reflective). However, more light might be needed to inspect a primer coat (less reflective) to get more contrast between reflections 48 and car body 12.

It is to be further understood that conventionally, vertically oriented portions 40 will be used for the sides of car body 12. More precisely, reflections 48 will be established up and down the sides of the car. In contrast, as shown in FIG. 2, reflections 48 might be established longitudinally along the hood and trunk. It is possible to have other shapes of illuminated portions 40. One stripe is possible or even shapes such as squares, checks, or nonlinear shapes are possible. Still further, if sets of illuminated portions 40 are used, they do not necessarily need to be parallel or identical. One example would be to taper the width of strip illuminated portion 40.

Further options would be to filter or otherwise change the color or type of light used to form reflections 48. For example, the color pink might provide a better analytical color for paint inspection of gray auto bodies 12 than normal fluorescent light. The visual spectrum of light used with station 30 could be limited according to design to increase the ability to distinguish flaws in bodies 12.

Figure 8:
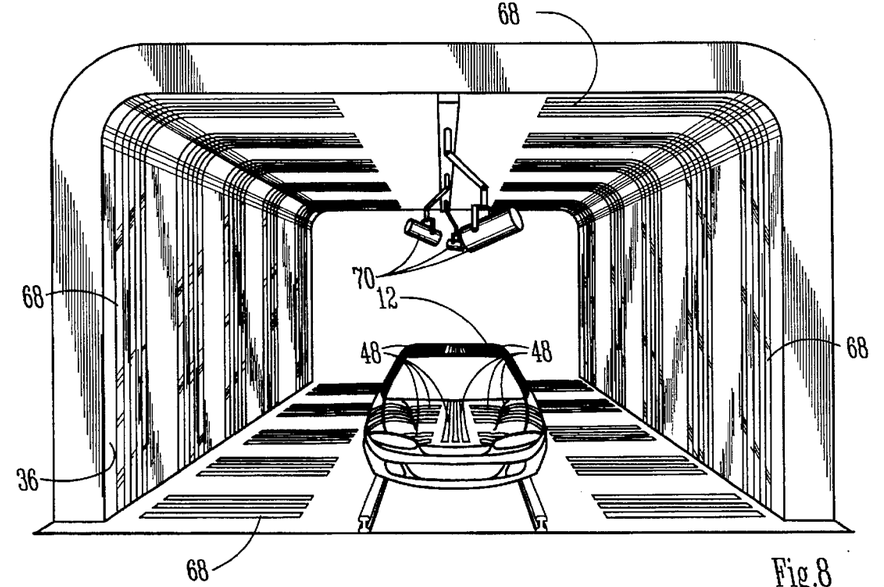
FIG. 8 is a perspective view of an alternative embodiment of a portion of a paint inspection station according to an embodiment of the present invention.

FIG. 8 shows another alternative with regard to the present invention. Instead of having translucent illuminated portions 40, side walls 36 and 38 could remain unreflective and light absorbing, but areas 68 could be of a diffusely reflecting material. For example, the sand blasted surface of clear acrylic could be painted white in areas 68. One or more light sources 70 could then be directed to shine on strips 68. A reflected image 48 could then be seen in body 12, but like previously described, a minimum amount of direct light would pass to body 12. Lights 70 would be directed onto diffusely reflective portions 68, not onto car body 12.

It will again be emphasized that the invention can be used not only with painted or coated surfaces, but also non-painted or non-coated bare surfaces. The primary limitation is that the surface must be specular or semi-specular.

It will be appreciated that the present invention can take many forms and embodiments. The true essence and spirit of this invention are defined in the appended claims and it is not intended that the embodiment of the invention presented herein should limit the scope thereof.

We claim:

1. A method of inspecting a specular or semi-specular surface of any object by a viewer comprising:

illuminating a pattern having at least one defined generally edge characteristic and a reference line which is generally perpendicular to the edge characteristic;

positioning the pattern relative to the object and the viewer so that the illuminated pattern is reflected in the surface of the object at an angle or angles incident to the viewer.

2. The method of claim 1 wherein the pattern consists of alternating lighter and darker sections.

3. The method of claim 1 wherein the pattern comprises at least one geometrical shape.

4. The method of claim 3 wherein a plurality of patterns are reflected in the surface of the object.

5. The method of claim 1 wherein the pattern is illuminated by back lighting.

6. The method of claim 1 wherein the pattern is illuminated by front lighting the pattern but not the object.

7. The method of claim 1 wherein the intensity of the illuminated pattern is adjustable.

8. The method of claim 1 wherein the size of the pattern is adjustable.

9. The method of claim 1 wherein the color of the illuminated pattern is adjustable.

10. The method of claim 1 wherein the pattern can be altered during an inspection.

11. The method of claim 1 wherein the defined edge characteristic is at least partially a straight line.

12. The method of claim 1 wherein the defined edge characteristic is at least in part a non-straight line.

13. An apparatus for inspecting a specular or semi-specular surface on an object comprising:

a generally non-reflective, light absorbing supporting surface for the object;

a generally non-reflective, light absorbing backdrop positioned adjacent to the supporting surface;

a light source; and the backdrop including at least one portion that can be illuminated by the light source;

the portion of the backdrop including a pattern having at least one defined generally edge characteristic and a reference line which is generally perpendicular to the edge characteristic;

so that the pattern can be reflected onto the surface of the object to assist in inspection of the surface.

14. The apparatus of claim 13 wherein the object is an automobile body with at least one coat of paint.

15. The apparatus of claim 13 wherein the object includes at least a portion which is wooden and which is coated with a protective coating.

16. The apparatus of claim 13 wherein the supporting surface comprises a platform for supporting the object.

17. The apparatus of claim 16 wherein the supporting surface includes an illuminated portion.

18. The apparatus of claim 13 wherein the light source comprises one or more lamps.

19. The apparatus of claim 18 wherein the light source includes a reflector.

20. The apparatus of claim 13 wherein the backdrop comprises a wall of material.

21. The apparatus of claim 20 wherein the wall borders both sides of the supporting surface.

22. The apparatus of claim 20 wherein the wall covers at least a substantial amount of the supporting surface.

23. The apparatus of claim 20 wherein the backdrop further comprises end walls which cover a substantial portion of ends of the supporting surface.

24. The apparatus of claim 13 wherein at least one portion comprises at least one geometrical shape.

25. The apparatus of claim 24 wherein the geometrical shape comprises at least one stripe.

26. The apparatus of claim 24 wherein the geometrical shape comprises a plurality of stripes.

27. The apparatus of claim 26 further comprising a plurality of non-reflective, light absorbing stripes separating the plurality of illuminated stripes.

28. The apparatus of claim 12 wherein the pattern comprises a plurality of portions positioned along the backdrop.

29. The apparatus of claim 28 wherein the plurality of portions comprise curved stripes.

30. The apparatus of claim 28 wherein the plurality of portions comprise tapered stripes.

31. The apparatus of claim 28 wherein the plurality of portions comprise generally horizontal sections.

32. The apparatus of claim 28 wherein the plurality of portions comprise generally vertical areas.

33. The apparatus of claim 13 wherein the surface is a non-coated surface.

34. A paint inspection station comprising:

a floor supporting a painted object to be inspected;

a canopy including at least opposite sides surrounding at least a substantial portion of opposite sides and top of the floor;

the floor and canopy having a generally non-reflective, light absorbing surface;

at least one of an illuminated portion and a light reflecting portion positioned on at least one of the floor and canopy, the said one of an illuminated portion and a light reflecting portion including a pattern having at least one defined generally edge characteristic and a reference line which is generally perpendicular to the edge characteristic;

so that a paint inspector can view a reflected image of the pattern in the object while standing on the floor under the canopy.

35. The station of claim 34 wherein the painted object is an automobile body.

36. The station of claim 34 wherein the canopy substantially encloses the painted object.

37. The station of claim 34 wherein one of the illuminated portion and light reflection portion is of a geometric shape having at least one straight edge.

38. The station of claim 34 wherein one of the illuminated portion and light reflecting portion comprise a plurality of spaced apart stripes.

* * * * *